US012611364B1

(12) United States Patent
Gellman et al.

(10) Patent No.: US 12,611,364 B1
(45) Date of Patent: Apr. 28, 2026

(54) SYSTEMS AND METHODS FOR DISPENSING MEDICATIONS AND SUPPLEMENTS

(71) Applicants:Charles Gellman, El Dorado Hills, CA (US); Brandon Woolsey, Redding, CA (US); Ignacio Garcia Perez, Betera (ES)

(72) Inventors: Charles Gellman, El Dorado Hills, CA (US); Brandon Woolsey, Redding, CA (US); Ignacio Garcia Perez, Betera (ES)

( * ) Notice: Subject to any disclaimer, the term of this patent is extended or adjusted under 35 U.S.C. 154(b) by 533 days.

(21) Appl. No.: 17/902,647

(22) Filed: Sep. 2, 2022

Related U.S. Application Data

(62) Division of application No. 16/600,429, filed on Oct. 11, 2019, now Pat. No. 11,554,081.

(51) Int. Cl.
| | |
|---|---|
| A61J 1/03 | (2023.01) |
| A61J 7/00 | (2006.01) |
| G07F 17/00 | (2006.01) |
| G16H 10/65 | (2018.01) |

(52) U.S. Cl.
CPC ............... A61J 7/0084 (2013.01); A61J 1/03 (2013.01); G07F 17/0092 (2013.01); G16H 10/65 (2018.01); *A61J 2200/30* (2013.01); *A61J 2205/10* (2013.01)

(58) Field of Classification Search
CPC ..... A61J 7/0084; G16H 10/65; G07F 17/0092
USPC .......................................................... 221/13
See application file for complete search history.

(56) References Cited

U.S. PATENT DOCUMENTS

| | | | |
|---|---|---|---|
| 9,579,264 B1 * | 2/2017 | Litton ................... | A61J 7/0481 |
| 11,554,081 B1 * | 1/2023 | Gellman ................ | G16H 10/65 |
| 2014/0097194 A1 * | 4/2014 | Lai ...................... | B65D 83/0454 |
| | | | 221/13 |
| 2015/0090733 A1 * | 4/2015 | Park ...................... | A61J 7/0481 |
| | | | 221/277 |
| 2016/0068328 A1 * | 3/2016 | 'T Lam .............. | B65D 83/0409 |
| | | | 53/244 |
| 2016/0128906 A1 * | 5/2016 | Baarman ................... | A61J 7/04 |
| | | | 221/13 |

(Continued)

*Primary Examiner* — Gene O Crawford
*Assistant Examiner* — Ayodeji T Ojofeitimi

(57) ABSTRACT

A medication dispensing device comprising a rotating platform configured for receiving a plurality of medication dispensing containments housing a plurality of pills comprising medication or supplements, and a scanner or user input for identifying the one or more medication containments and receiving data specific to the medication or supplements provided therein, wherein the medication containment has a lower surface with a dispensing opening and pill capture head sized according to at least one dimension of the plurality of pills contained therein, and a medication sweeper disposed above the pill capture head and between the plurality of pills so as to selectively direct is single pill out the dispensing opening while blocking a remainder of the plurality of pills in the containment. A motor-driven first gear is coupled to the pill capture head and medication sweeper such that rotation of the gear affects rotation of the pill capture head with respect to the medication sweeper to dispense the single pill, wherein the motor receives commands from data acquired by the scanner to affect dispensing of the single pill.

20 Claims, 14 Drawing Sheets

(56) References Cited

U.S. PATENT DOCUMENTS

2016/0324727 A1 * 11/2016 Waugh .................. G16H 20/13

* cited by examiner

SYSTEMS AND METHODS FOR DISPENSING MEDICATIONS AND SUPPLEMENTS

CROSS-REFERENCE TO RELATED APPLICATIONS

This application is a divisional application of U.S. patent application Ser. No. 16/600,429, filed on Oct. 11, 2019, which claims priority to, and the benefit of, U.S. provisional patent application serial number to U.S. Provisional Patent Application No. 62/744,218 filed on Oct. 11, 2018, also incorporated herein by reference in its entirety.

TECHNICAL FIELD

The present disclosure relates generally to dispensing of medicaments and supplements, and more particularly to an automated system and method for maintaining adherence for dispensing of medicaments and supplements.

BACKGROUND

Medication adherence refers to whether patients take their medications as prescribed (e.g., twice daily), as well as whether they continue to take a prescribed medication. Medication non-adherence is a growing concern to clinicians, healthcare systems, and other stakeholders (e.g., payers) because of the mounting evidence of its prevalence, and associated adverse outcomes and higher costs of care.

As should be appreciated, there is a continuing need to improve medication adherence, and in particularly a need for an automated system that is capable of tracking dispensing of multiple medications from the same dispensing device, with visual confirmation that the patient is dispensed the correct medication at the correct time, and that the patient indeed ingests the medication.

SUMMARY OF THE DISCLOSURE

An aspect of the present description is a medication adherence system and method configured to increase compliance results and provide real time data insights to clinicians that may improve patient outcomes.

In one embodiment, system comprises a one or more pill cap assemblies that are configured to mate with an existing prescription pill container (e.g. off-the-shelf 40 dram container) and be inserted into a dispensing device comprising mechanized carousel for automated dispensing of one or more containers of medicament. The system may include a backend cloud system and a Web and/or mobile application.

In a preferred configuration, the pill cap assembly is configured to capture a pill of a specified size, and includes a pill capture piece that has a fixed depth and width. One or more pill capture spacers may be used to match, or closely match a specified pill dimension (e.g. height) and a slot is provided that matches one or more other dimensions of the pill (e.g. depth, width, radius, etc.) width. A sweeper component is provided, and may include a fixed radius that corresponds with the pill capture depth so that only one pill is captured and dispensed, while blocking and repositioning remaining pills within the container. Outer cap spacers may be provided to allow an outer cap structure to have the same height configuration as the pill capture spacers. A cap end is provided with a slot to allow the pill to be extruded from the device for dispensing. In one embodiment, a plastic ring is inserted between the pill cap assembly and container to allow for similar childproof functionality as standard prescription caps (e.g. the user applies a downward pressure to the cap assembly while turning the cap assembly in order to remove the cap).

In a preferred embodiment, the cap assembly comprises an identifier, such as an integrated RFID tag or chip, bar code, or like identifier that details information pertinent to the medication, patient, or prescription (e.g. one or more of the medication name, dosage amount, frequency of dosing, etc.), which is encoded onto the RFID.

In another embodiment, the system includes an integrated platform that automatically recognizes medications when inserted in the device via a cartridge configured to house medications in numerous types of shapes or sizes.

In a preferred embodiment, the system, in any of the above configurations, is configured to recognize the name of the medication, dosage, frequency and potential adverse events with other medications loaded in the device for the patient. One or more electric motors drive the unit into the desired position and then rotate the pill cap assembly or cartridge to then dispense the appropriate dose of medication or medications from the pill cap assembly or cartridge into a cup or catching tray. One or more sensors or cameras are preferably included to track the dispensing of the medication from the unit and then track the medication travel from the unit to the individual's mouth. The device accounts for all medications within the containers/cartridges and can be configured to order new medications for refill prior to running out of any one medication.

In one aspect, the system includes an enclosure, a pill cup, a screen and/or IOS/Android/Windows/Web etc. application, one or several optional buttons for user interface, a rotating platform, two motors, one or more rotary encoders or other motion/position sensors, one or more cameras, an RFID receiver, a control gear and one or more pill cap assemblies/cartridges.

In another aspect, the system described herein comprises four primary modules: an application interface for communication with the device, (e.g. external device such as phone, web, and/or desktop application), the cloud, pill cap assemblies and the device itself.

In one embodiment, the medication adherence dispensing system comprises two motors that are asynchronous to align mechanisms that dispense pills of all shapes and sizes. This is enabled by application software configured to control the mechanics and electrical components that move the device and control data rights. Cartridges loaded in the device are recognized by the unit and will dispense medications based upon frequency recommendations of the prescribing clinician.

Further aspects of the technology described herein will be brought out in the following portions of the specification, wherein the detailed description is for the purpose of fully disclosing preferred embodiments of the technology without placing limitations thereon.

BRIEF DESCRIPTION OF THE DRAWINGS

The technology described herein will be more fully understood by reference to the following drawings which are for illustrative purposes only.

DETAILED DESCRIPTION

Figure 1:
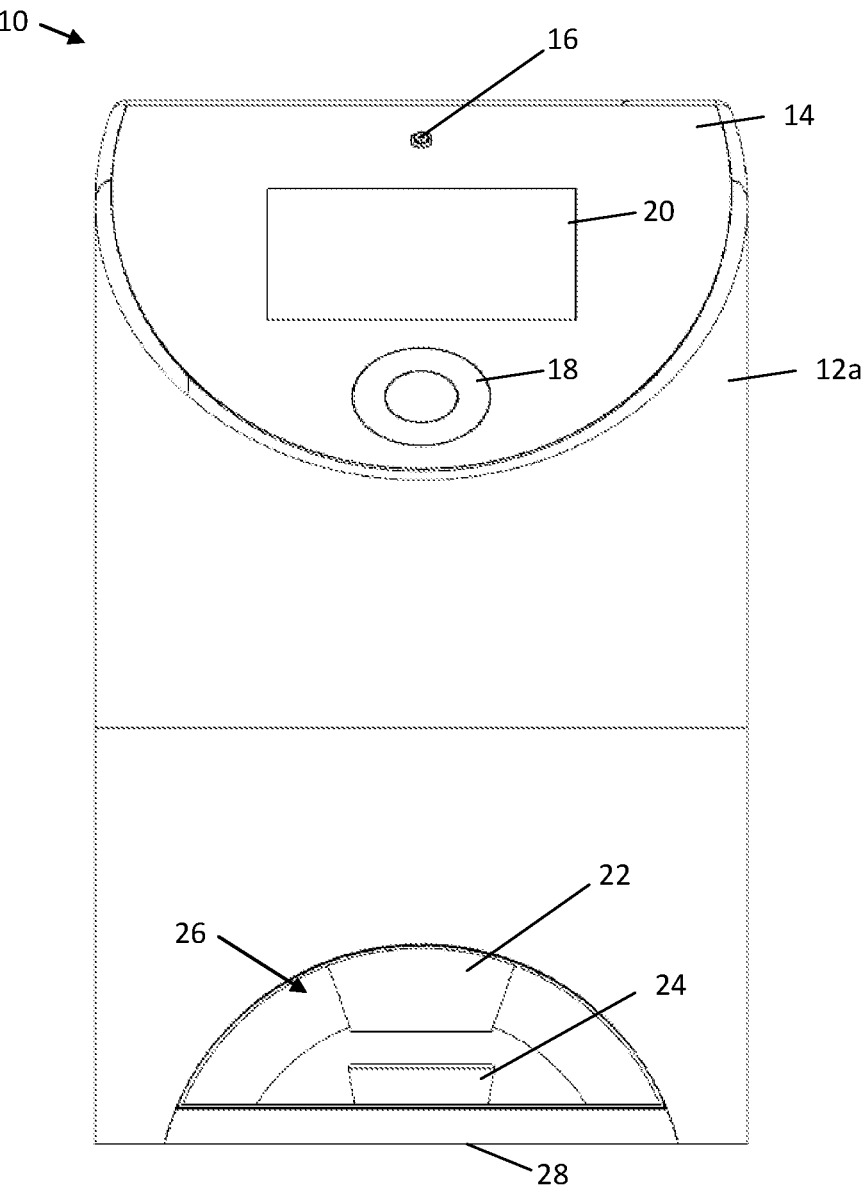
FIG. 1 is a front view of a medication adherence dispensing device incorporating a pill-cap assembly for use with an existing pill container in accordance with the present description.

FIG. 1 through FIG. 9 show a first embodiment of a medication adherence dispensing device 10 incorporating a pill cap/container assembly 30 for use with an existing pill container 32 in accordance with the technology of the present description. FIG. 10 through FIG. 14 show a cartridge-based medication adherence dispensing device 200 in accordance with the technology of the present description. It is appreciated that components of devices 10 and 200 may be variably interchanged, where appropriate.

Figure 2:
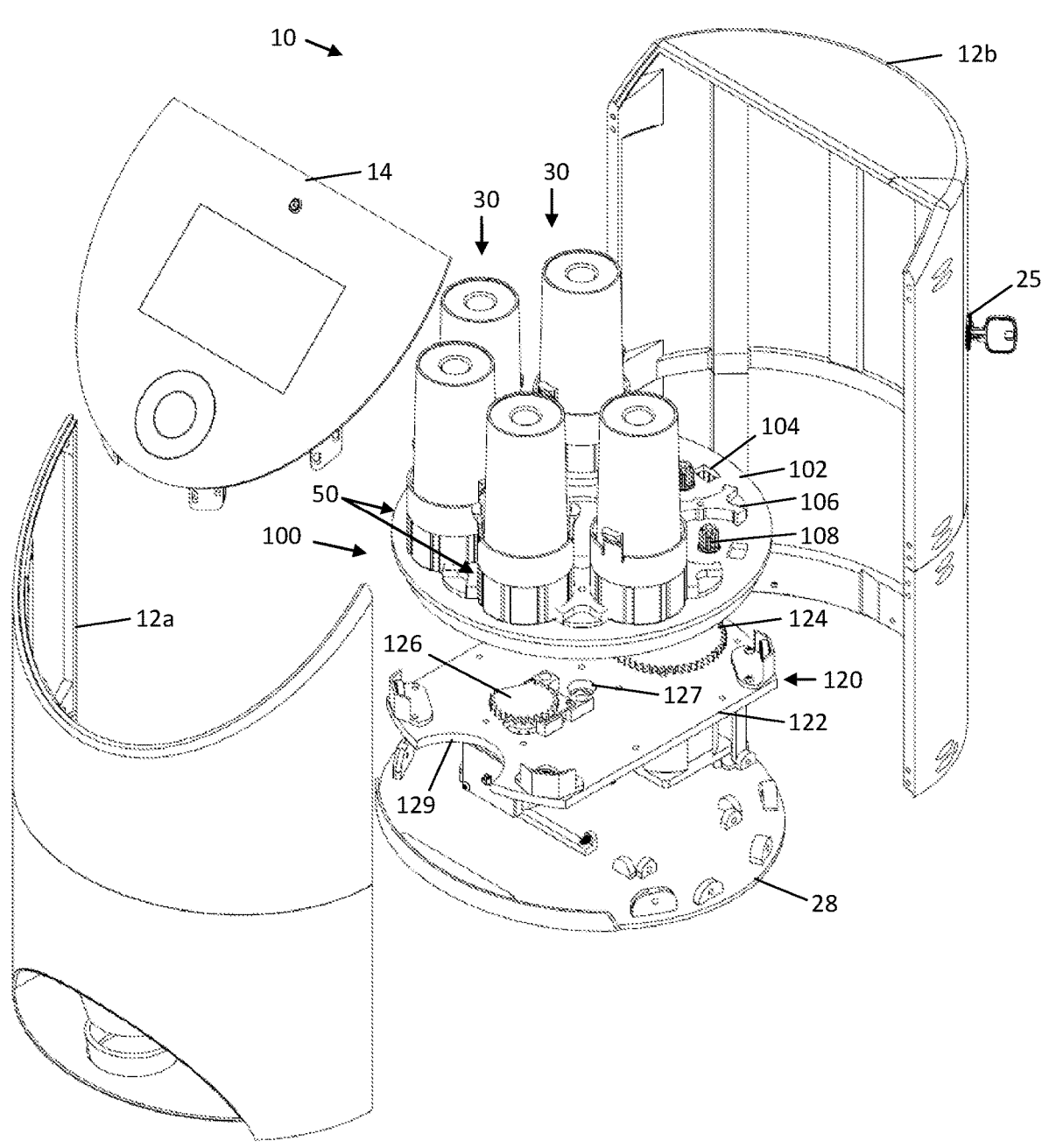
FIG. 2 shows an exploded perspective view of the medication adherence dispensing device of FIG. 1.
Figure 3:
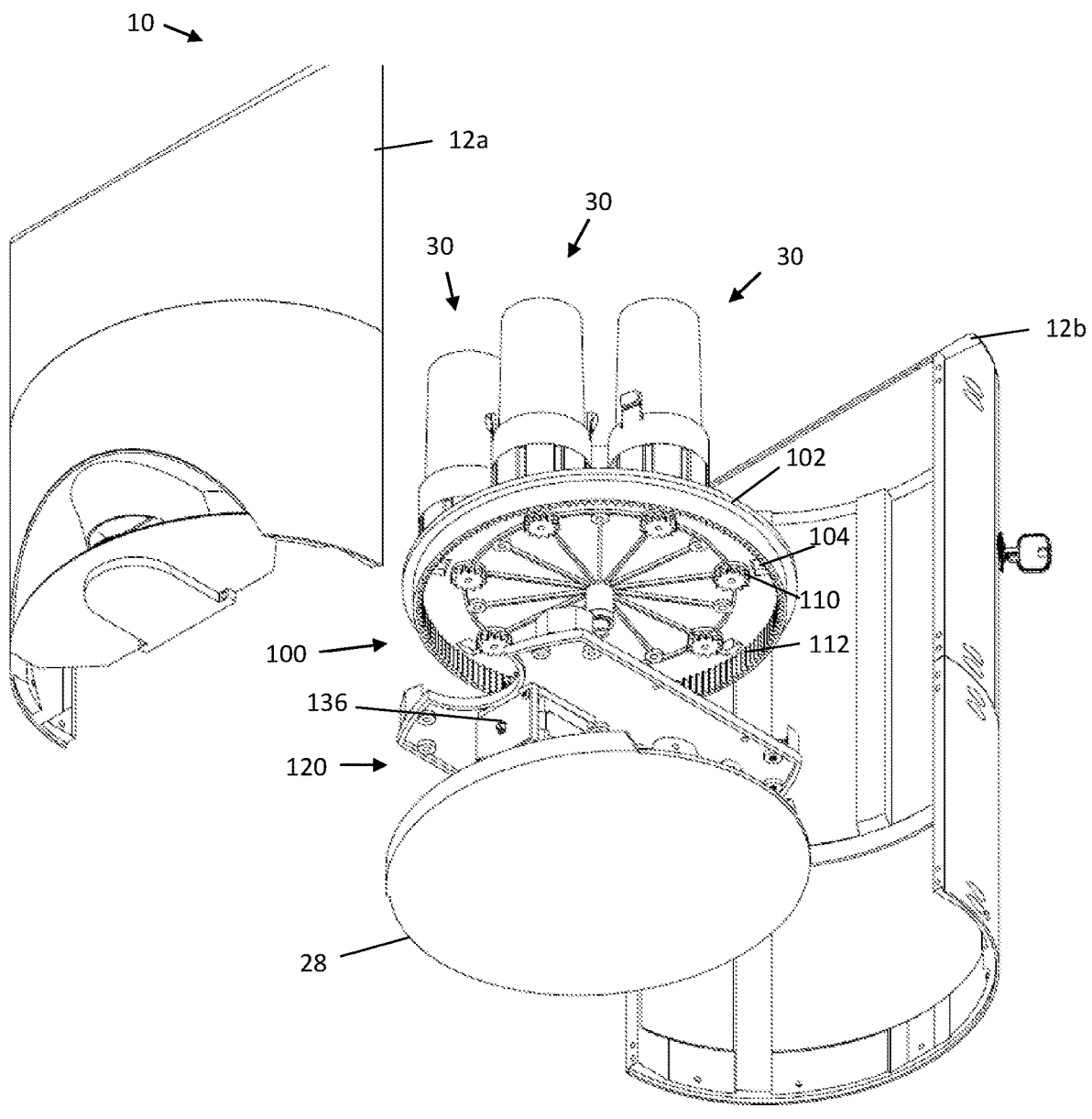
FIG. 3 shows another exploded perspective view of the medication adherence dispensing device of FIG. 1.
Figure 4:
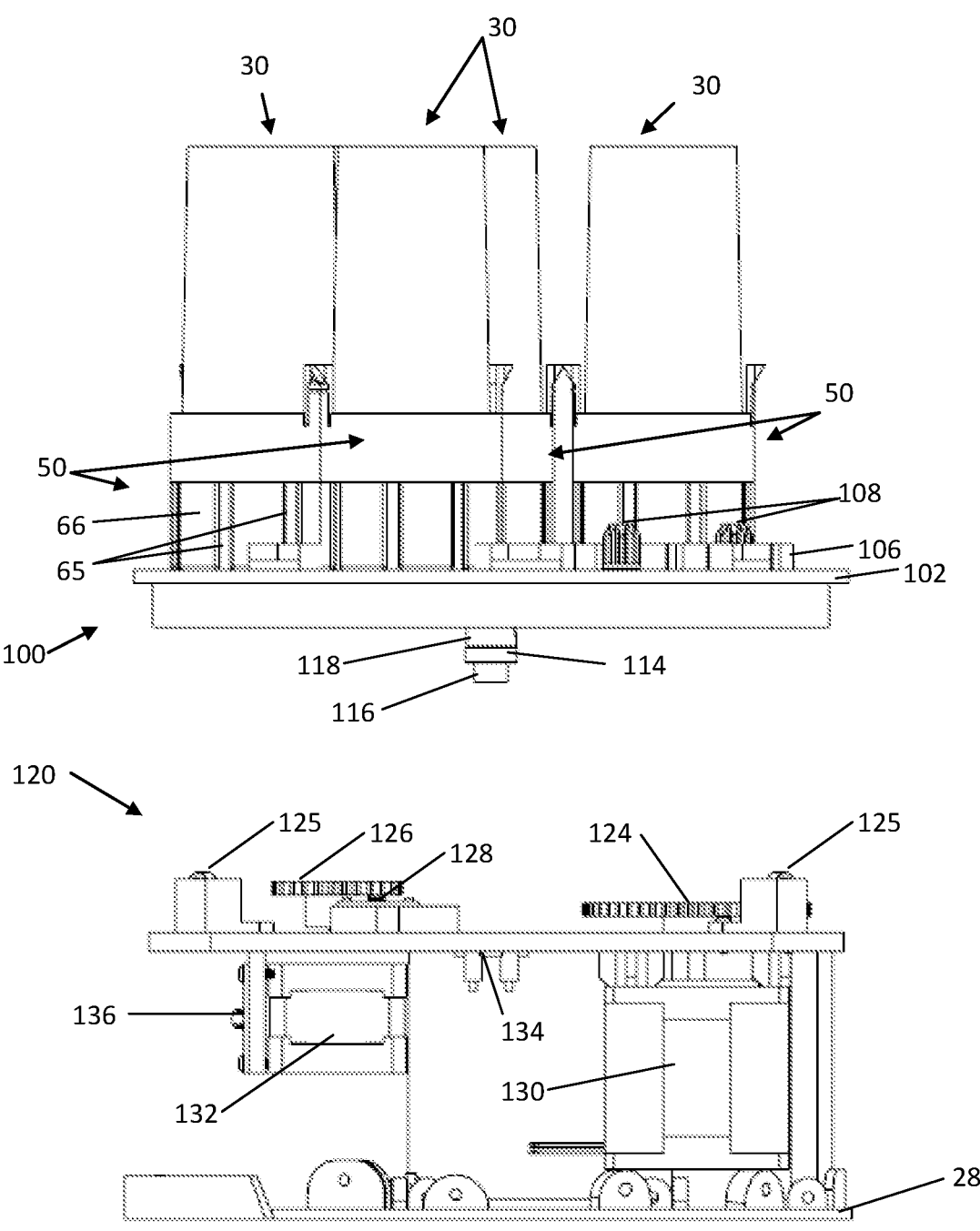
FIG. 4 shows an exploded side view of the medication adherence dispensing device of FIG. 1, with outer housing removed.

Referring now to FIG. 1, a front-side view of a medication adherence dispensing device 10 incorporating a pill-cap assembly for use with an existing pill container is depicted. For clarity, perspective views of the dispensing system 10 in an exploded configuration are provided in FIG. 2 and FIG. 3, and FIG. 4 shows an exploded side view of the dispensing device 10, with outer housing removed for clarity. Dispensing device 10 comprises an outer casing that is defined by a front housing member 12*a*, rear housing member 12*b* (FIG. 2), bottom platform 28, and a front panel 14 that contains a display 20, optional buttons/user interface 18, and camera 16. The front housing member 12*a* comprises a dispensing recess 26 with a pill dispensing channel 22 configured to deliver the medication to pill cup 24 that rests on bottom platform 28.

The dispensing display 20 may comprise a touch screen that allows for user/patient interface with the dispensing device 10, along with or alternatively to option buttons/input 18. In addition to or alternatively to the display 20, the user or patient may interface with the dispensing device 10 via an application loaded on an external device and/or cloud-based server (see external device 160 and server 162 in FIG. 9) to provide some or all of the interface functionality of display 20/buttons 18. Such functionality includes, but is not limited to: adding new medications to dispense, setting the schedule at which the medications will be dispensed, entering patient information, confirming the dispensing of said medication, etc.

Front panel 14 may also comprise logic and other circuitry for operation and or control of the dispensing device 10, such as controller 150 (FIG. 9) that is coupled to the various components of the dispensing device 10 (e.g. via wiring/leads (not shown) and/or external devices).

Referring to FIG. 2 and FIG. 3, the rear housing member 12*b* may comprise a hinged door that swings open to allow access to the internal components of the dispensing device 10 and insertion/removal of the pill cap/container assemblies 30. A keyed lock 25 or similar locking mechanism may be provided to inhibit access to the internal components or medication contained within the casing.

A pill-dispensing carousel assembly 100 is provided for insertion of one or more pill cap/container assemblies 30, each having dedicated medications for dispensing to the patient. The carousel assembly 100 comprises a rotating platform 102 with an upper surface for the one or more pill cap/container assemblies 30 to be positioned at any of several locations on the rotating platform 102. FIG. 2 and FIG. 3 show five pill cap/container assemblies 30 installed at dedicated locations from a circular array of seven locations (two not occupied) on the platform 102. However, it is appreciated that the array may comprise any number of locations (e.g. two or more) for installation of various cap/container assemblies 30.

Each pill cap/container assembly 30 is formed by attaching a dedicated pill cap assembly 50 to a container 32, wherein the pill cap assembly 50 comprises an identifier, such as an integrated RFID tag or chip 40, bar code, or like identifier that details information pertinent to the specific medication provided in the container 32 (e.g. data relating to the prescription (e.g. one or more of the medication name, dosage amount, frequency of dosing, etc.) and/or patient. Preferably, this information is encoded onto the RFID 40. In a preferred embodiment, one or more RFID receivers/readers (see RFID reader 140 in FIG. 9) are disposed at a location (e.g. a centralized location on platform 102) to read the individualized/encoded RFID's 40 (FIG. 5 through FIG. 6) on the respective pill cap/container assemblies 30 and collect the information and for identification of the medication and corresponding location of the associated cap/container assembly 30.

To attach to the rotating platform 102, each cap/container assembly 30 in concentrically positioned over a respective pill cap mating gear 108and retained from rotation via brackets 106. The rotating platform 102 also comprises an array of pill dispensing slots 104 that are offset from the rotation axis of the pill cap mating gears 108. The carousel assembly 100 is configured to be positioned on an elevated gear platform 122 of motion assembly 120, which houses pill dispense gear 126 and carousel positioning gear 124. The carousel assembly 100 is rotationally mounted to the elevated gear platform 122 via a bearing 114 on pin 118 (FIG. 4) that extends from the underside of rotating platform 102 to mate with aperture 127 (FIG. 2) and through the elevated gear platform 122. The periphery of rotating platform 102 is supported by a set of wheels 125 that are rotatably mounted to the top surface of elevated gear platform 122. Carousel positioning gear 124 is located on the elevated gear platform 122 so as to interface with matching teeth 112 (FIG. 3) on the bottom surface of rotating platform 102, such that rotation of carousel positioning gear 124 (via operation of carousel motor 130) drives motion of rotating platform 102 about pin 118. Correspondingly, the pill dispense gear 126 is located on the elevated gear platform 122 such that it is configured to variably mate with one of the selected the pill dispense mating gears 110 (FIG. 3) located in an array on bottom surface of rotating platform 102, wherein the array is matched and rotationally coupled to the pill cap mating gears 108 on the upper surface of the rotating platform 102. Pill dispense gear 126 has a flat or non-toothed edge along a portion of its circumference to allow for rotation of the platform 102 into respective pill cap/container assembly 30 locations without interference with the mating gear 110 coupled to the respective pill cap/container assembly 30. Upon rotation of the pill dispense gear 126 (via operation of dispensing motor 132), the selected pill dispense mating gear 110 and corresponding pill cap mating gear 108 rotate, which drives dispensing of medication from the desired pill cap/container assembly 30, as will be explained in further detail below.

Referring to FIG. 4, the distal end of pin 118 comprises a magnet 116 that is configured to extend through elevated gear platform 122 and align with a sensor 134 (e.g. rotary encoder, Hall-effect sensor, or like device) on the bottom surface of the elevated gear platform 122. The magnet 116 is rotationally clocked with the rotating platform 102 and the position of the individual pill cap mating gears 108 such that the rotational position of the magnet 116 allows the rotary encoder 134 to identify the position of the rotating platform 102 and relative positions of the cap/container assemblies 30. This allows the device 10 to identify where each respective pill cap/container assembly 30 is located in order to move the carousel assembly 100 to the correct position to dispense the appropriate medication from among a plurality of medications.

As mentioned above, to dispense a pill/medication, the rotating platform 102 rotates to place a specific cap/container assembly 30 in the "dispense" position for dispensing the desired medication. This "dispense" position assures that the pill dispense mating gear 110 coupled to the cap/container assembly 30is now mated with the control gear (pill dispense gear 126). The rotational location of the pill dispense gear 126 may also be tracked with a sensor 128 (e.g. rotary encoder, Hall-effect sensor, or like device) to determine clocking of gear 126. Rotation of the pill dispense gear 126affects rotation of mating gear 110/108, which rotates the pill capture head to pick up a pill in the capture slot and then keep rotating until the pill falls out from the cap/container assembly 30and through the pill dispense channel 22 formed through notch 129 in the gear platform 122 (FIG. 2), and gets placed in the pill cup located on the exterior of the device where the user can then take his/her medication. As the pill falls, it passes a sensor 136 (e.g. optical sensor such as an IR light and photodiode shown in FIG. 3 and FIG. 4) to allow for indication of whether a pill is successfully dispensed, as well as tally the number of pills being dispensed. To ensure that the dispensed pill was ingested, camera 20 may take an image or video, and store image/video data in memory 156 or cloud-based server 162 (see FIG. 9). Application software 154, which may be implemented locally from memory 156 or externally from cloud-based server 162, may also include face recognition functionality to confirm the specified patient has administered the dose.

It is appreciated that while the sensing modalities detailed above (e.g. IR sensors, Hall effect sensors/encoders, etc.) are particularly suited for the use with specific applications detailed herein, any number of different sensor types or modalities may be implemented as available in the art. For example, sensors may include: tactile sensors such as switches, potentiometers, etc.; optical sensors such as photocells, IR sensors, etc.; and magnetic sensors such as Hall effect sensors, or the like.

Figure 5:
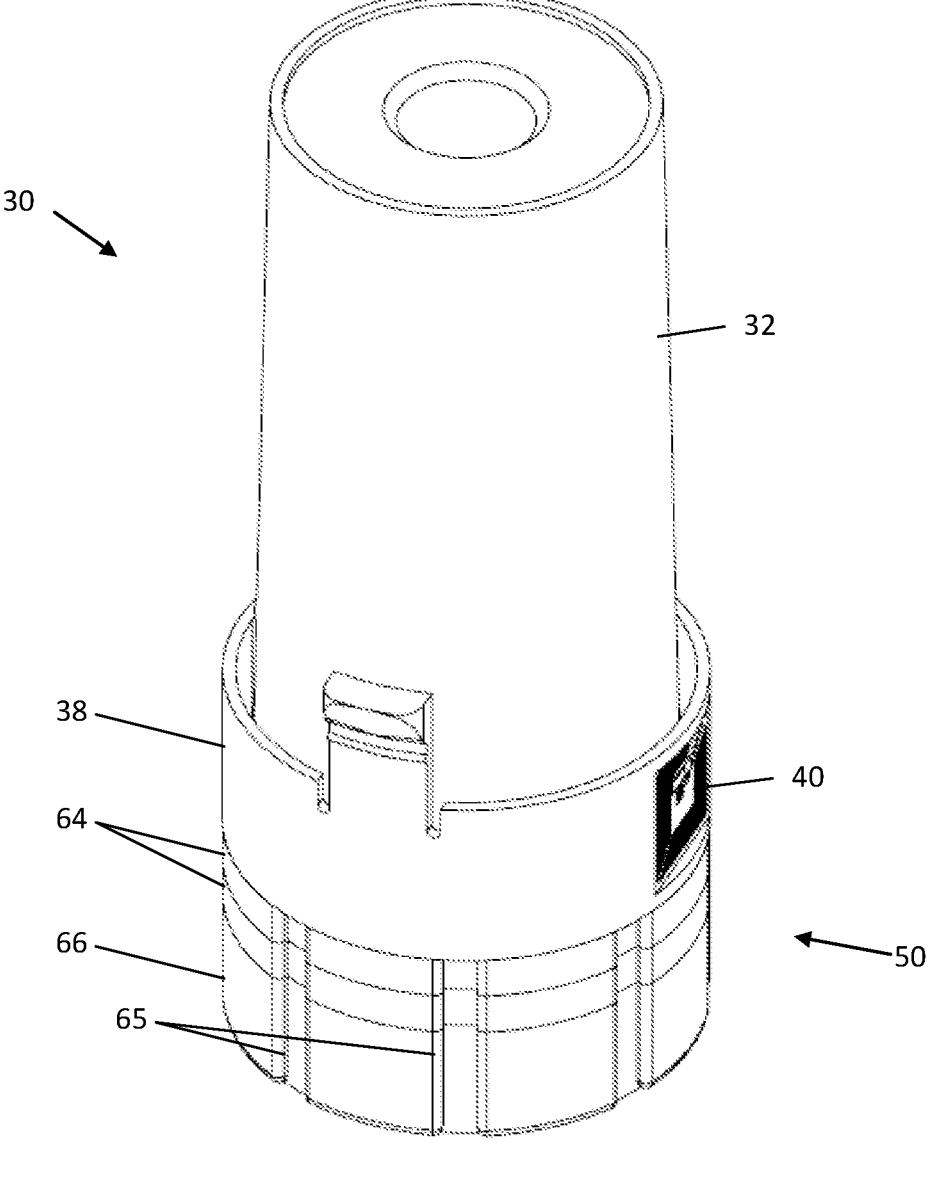
FIG. 5 shows an assembled pill cap assembly installed on an existing 40 dram container in accordance with the present description.
Figure 6:
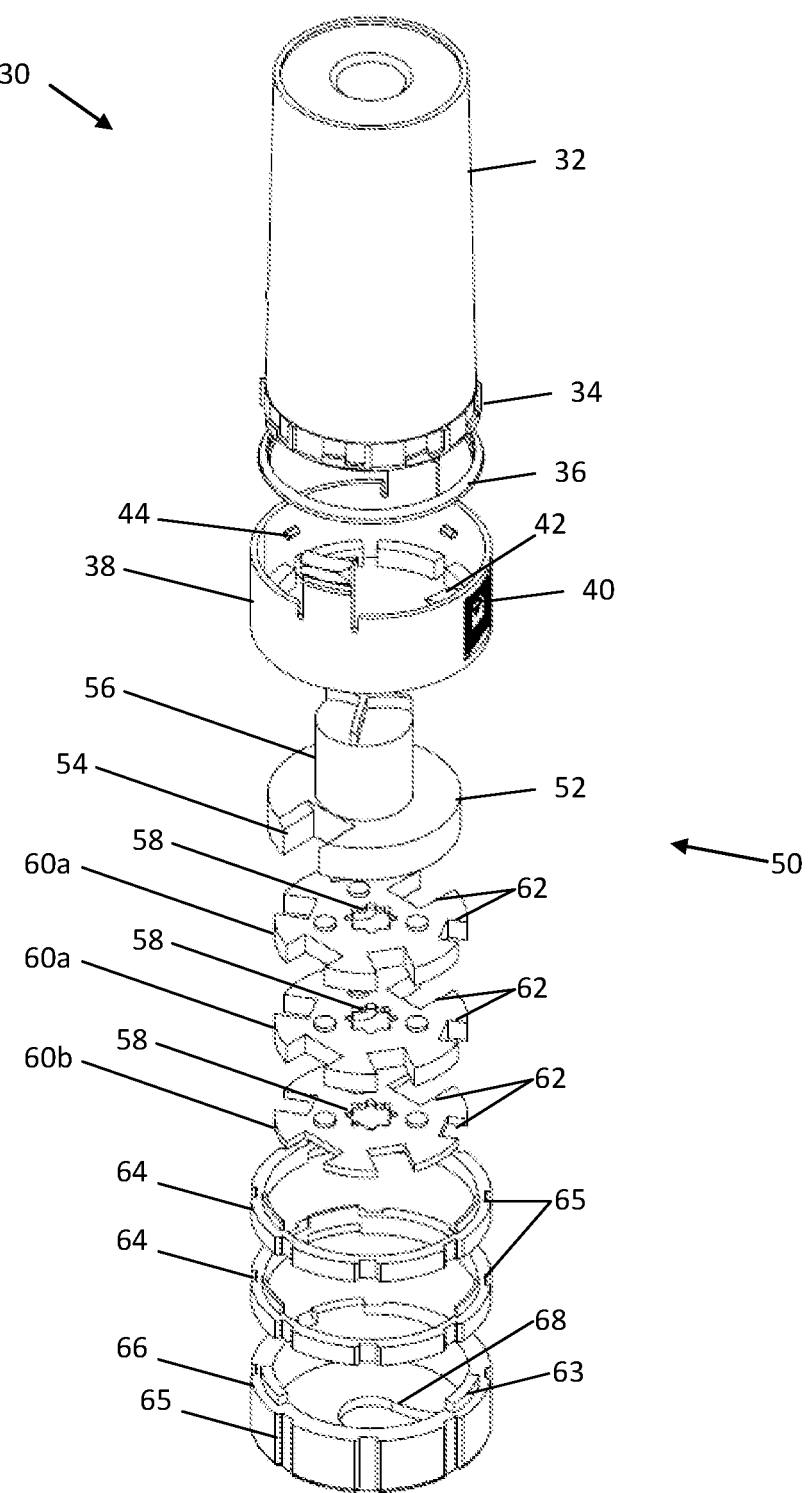
FIG. 6 shows an exploded perspective view of the pill cap/container assembly of FIG. 5.
Figure 7:
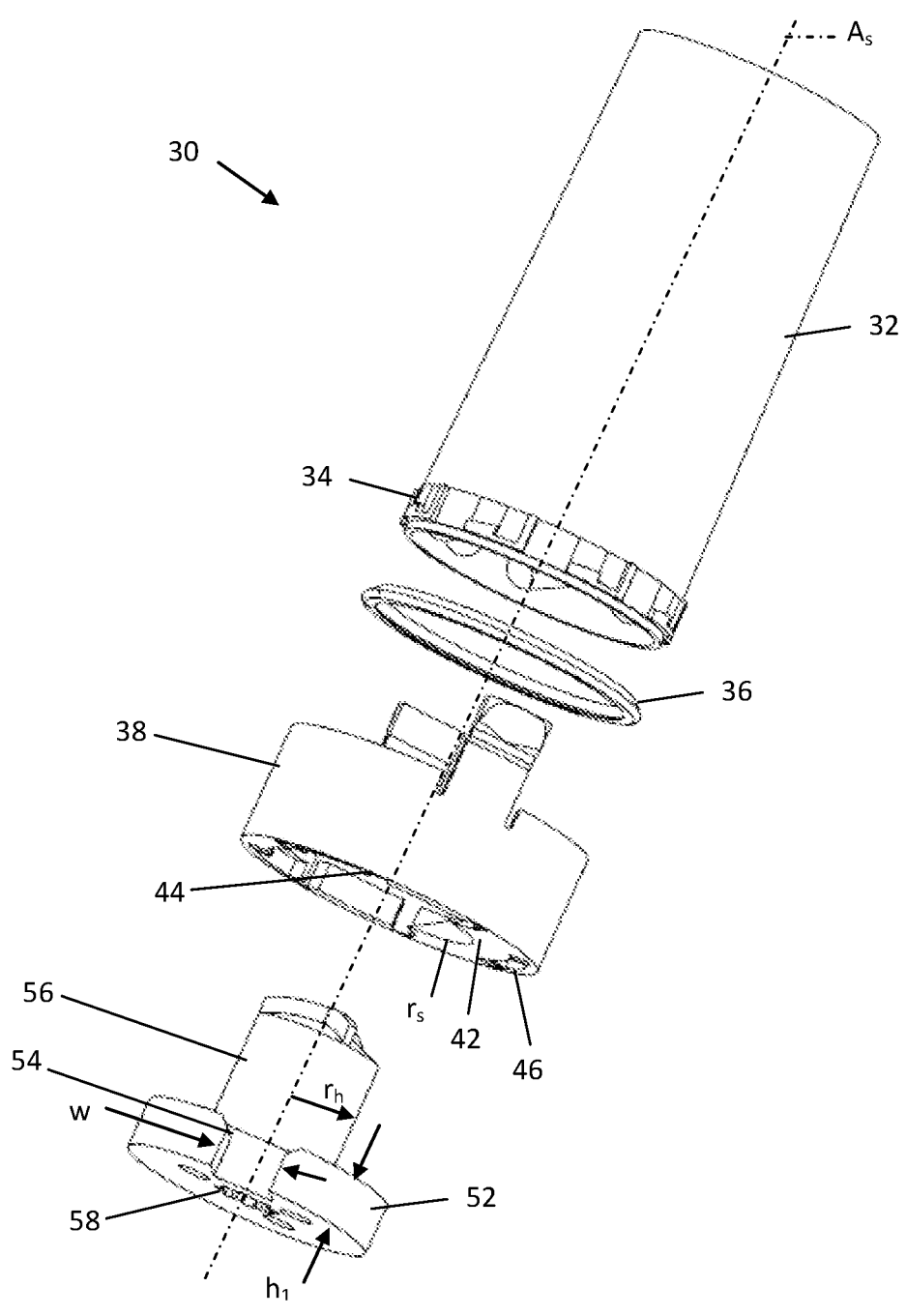
FIG. 7 shows another exploded perspective view of a few of the components of the pill cap/container assembly of FIG. 5.

FIG. 5 shows an assembled pill cap/container assembly 30 installed on an existing medication container 32 in accordance with the technology of present description. For clarity, perspective views of the pill cap/container assembly 30 are provided in FIG. 6 and FIG. 7, with side cut-out view of the assembled pill cap/container assembly 30 provided in FIG. 8. Each pill cap/container assembly 30 is formed by attaching a dedicated pill cap assembly 50 to an existing container 32. In one method of use, installation may simply comprise removing an existing cap off the container 32, and replacing it with a specified pill cap assembly 50. In one embodiment, the platform 102 is sized to receive and the pill cap assembly 50 is sized to attach to a specified off-the shelf container (e.g. 40 standard Dram pill container). However, it is appreciated that other sized containers (e.g. 20 Dram, 30 Dram, 60 Dram, etc.) may also be used. In one embodiment, the brackets 106 for rotationally retaining the container 32 on the rotating platform are set to a specific size (e.g. 40 Dram). Alternatively, the brackets 106 may slide or reciprocate on platform 102 to allow for smaller or larger container sizes. The pill cap assembly 50 preferably comprises an identifier 40, e.g. integrated RFID tag or chip, bar code, or the like, which is encoded with information pertinent to the specific medication provided in the container 32, e.g. one or more of the medication name, fulfillment facility, dosage amount, pill number, frequency and timing of dosing, or data relating to the prescription and/or patient. This information is preferably uploaded to the dispensing device 10 via scanner 140 (e.g. RFID reader 140 or like device configured to read data from identifier 40, see FIG. 9) to create the proper ingestion schedule and log the location of the medication within the carousel assembly 100. While the RFID 40 may be located on any location on the pill cap/container assembly 30, a preferred location shown in FIG. 5 through FIG. 7 is on an outer surface of the pill cap sweeper 38. If reader 140 is not available or operational, the user may input identifying information (e.g. bar code number, etc.) via manual input (e.g. with display 20, buttons 18) or through interface with an external device.

In a preferred embodiment, each pill cap assembly 50 is specifically configured to interface with the form (e.g. shape, size, etc.) of the particular medication it is to dispense. For some pills (e.g. pills not having significant height to width), the pill cap assembly 50 will simply include three concentrically aligned parts (about central rotation axis As shown in FIG. 7) in the form of the pill cap sweeper 38, an end cap 66 and a pill capture head 52 that is rotatably disposed within the confines of the cavity formed by the cap sweeper 38 and end cap 66 when extended. End cap 66 comprises a dispensing slot 68 configured to allow sequential and selected dispensing of pills.

Because of pill variability, one or more spacers (e.g. pill capture spacers 60a/60b and end cap spacers 64) may be concentrically aligned with the aforementioned parts to provide more depth to the pill capture cavity. Locking tabs (e.g. tab 63 on end cap 66 shown in FIG. 6) and corresponding keyed recesses (e.g. recess 46 in pill cap sweeper 38 shown in FIG. 7) are provided in the mating parts so that pill capture spacers 60a/60b and pill capture head 52 are rotationally locked to move in concert, and end cap spacers 64 and end cap 66 are all rotationally locked with respect to each other.

Figure 8:
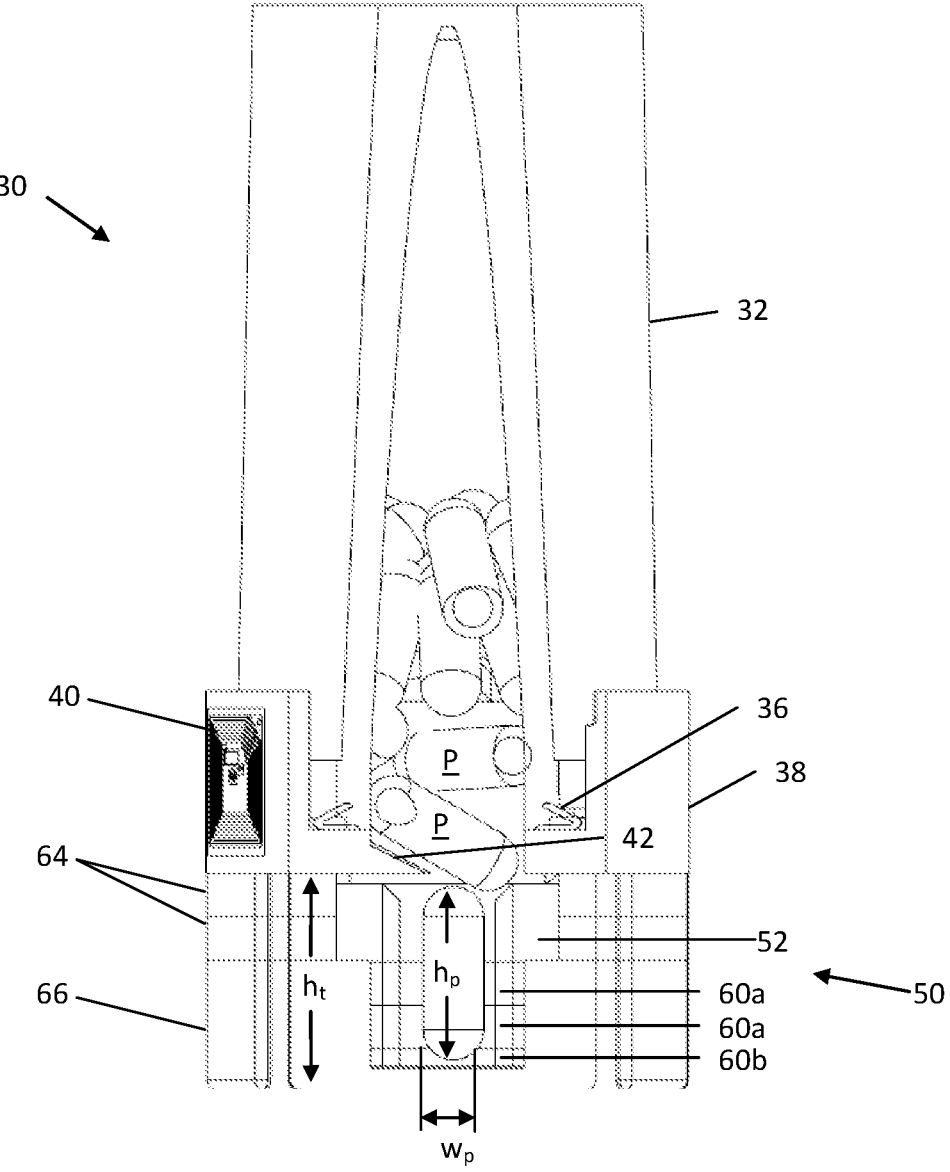
FIG. 8 shows a side cut-out view of the assembled pill cap/container assembly of FIG. 5.

The pill capture head 52 is shaped and sized with a cylindrical head 56 having radius rh, and a slotted base having a larger radius that generally matches or is slightly smaller than the radius of the inner cavity of end cap 66. Referring to FIG. 7 and FIG. 8, the cylindrical head 56 radius $r_h$ and width w and height $h_1$ of offset slot 54 are sized to roughly match the radius or width/depth of the medication (pill P) so that only one pill may fit between the inner pill cylindrical head 56 and the end cap 66 inner wall. One or more capture spacers (e.g. two 5 mm spacers 60a and one 1 mm spacer 60b are shown in the exemplary configuration in FIG. 6) may be provided to extend the height of the cavity to accommodate for more elongate pills; i.e. the number of spacers used, if at all, is a function of on the height of the pill $h_p$. The pill capture head 52 and pill spacers 60a/60b, when press fit together, form height h, such that when rotated only allow a single pill to be picked up (i.e. received in slot 54) for dispensing (see FIG. 8). In one exemplary embodiment, the slot height h, =pill height $h_p$+~0.3 mm, and slot width w=pill width $w_p$+$w_p$/10 (pill depth, if different, follows same formula as pill width). To minimize on the number of tooled parts, each spacer 60a/60b may comprise a number of different sized slots 62 that may correspond with and can be rotated in place to match the size of slot offset 54 (which is sized according to a particular pill size as detailed in the exemplary formulas above).

As seen in FIG. 7, the pill capture head 52 has a starred recess 58 (which may also match through-hole 58 in spacers 60a/60b) on its lower surface that mates with the pill cap mating gears 108 such that rotation of pill cap mating gears 108 drives rotation of the pill capture head52. As the pill capture head52 rotates with respect to the pill cap sweeper 38 (which remains fixed in motion along with end cap 66 and container 32) a radially inward projecting sweeper tab 42 directs and moves a single pill P to align with offset slot 54 see FIG. 8, such that the single pill is captured in the offset slot 54 for dispensing. Sweeper tab 42 has an internal radius and ramp angle (generally less than 45 degrees and between 25 degrees and 45 degrees) configured such that and when assembled it is located and affixed directly above the pill capture head 52 and aligned over the dispensing slot 66 of the end cap 38 such that it orients and directs a single pill P into slots 54/66 while blocking other pills in the container so only one pill falls through and is dispensed at a time.

As seen in FIG. 6, pill cap sweeper 38 has inner protrusions 44 that are configured to rotationally engage and lock orientation with end 34 of the pill container 32. A plastic ring 36 is preferably inserted between the pill cap assembly 50 and container 32 to allow for similar childproof functionality as standard prescription caps (e.g. the user applies a downward pressure to the cap assembly 50 while turning the cap assembly in order to remove the cap). The end cap 66 and cap spacers 64 preferably comprise longitudinal grooves 65 that when positioned within brackets 106 (FIG. 2) act to lock the pill cap/container assembly 30 in a fixed rotational orientation with respect to the rotating platform 102 such that torque applied to pill dispensing gear 108 only results in rotational motion of the pill capture head 52 and associated spacers (if used).

Figure 9:
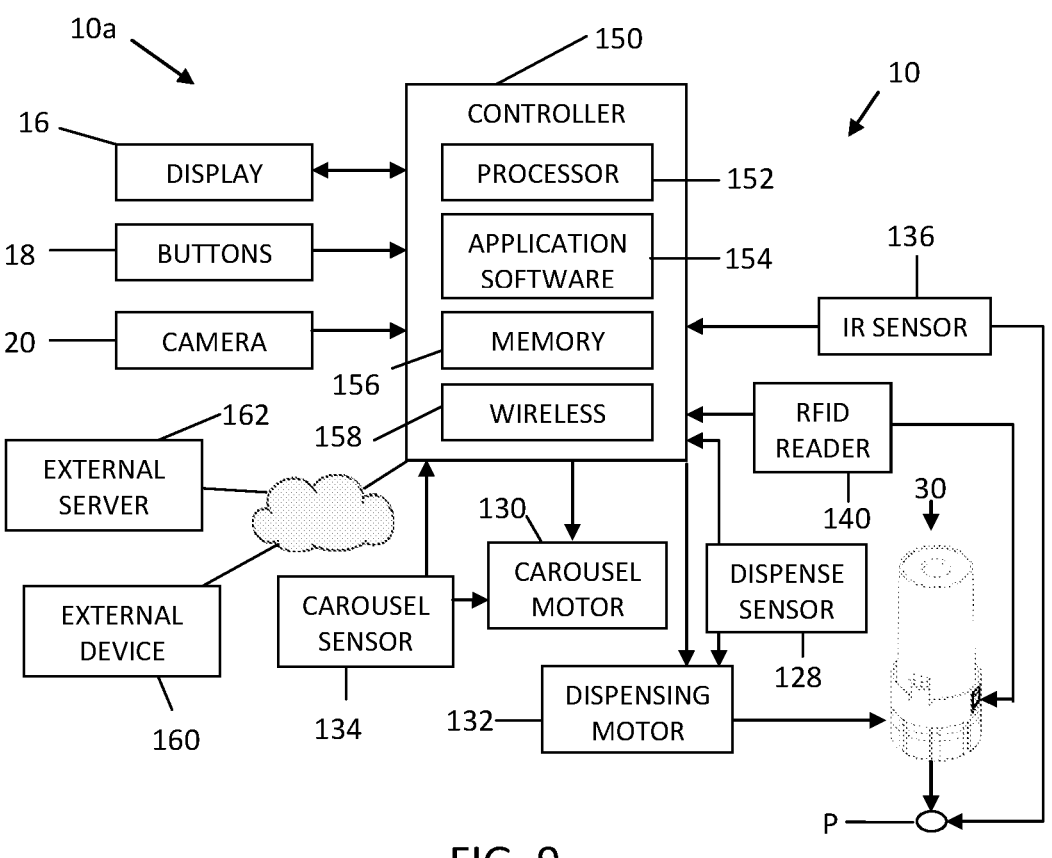
FIG. 9 shows a schematic system diagram illustrating various components of the medication adherence dispensing system for use with the device of FIG. 1.

FIG. 9 shows a schematic system diagram illustrating various components of a medication adherence dispensing system 10a. While the system 10a is illustrated for use for use with medication adherence dispensing device 10 and associated pill cap/container assembly 30 illustrated in FIG. 1 through FIG. 8, it is appreciated that many of the components detailed in FIG. 9 may be applicable or interchanged with the cartridge-based medication dispensing device 200 illustrated in FIG. 10 through FIG. 14. For purposes of this description, the cartridge 230 of dispensing device 200 and pill cap/container assembly 30 of dispensing device 10 are broadly referred as medication dispensing containments.

Dispensing device 10 preferably comprises a controller 150 that includes electronics/logic in the form of a processor 152 and application software 154 comprising code or machine-readable instructions stored in memory 156, the software 154 being executable on the processor 152 for controlling and communicating with the various components of the dispensing device 10, e.g. sending commands/data to operate carousel motor 130, dispensing motor 132, camera 20, display 16, RFID reader 140, etc., and receive data from IT sensor 136 relating to dispensing of pill P, dispensing sensor (e.g. encoder) 128, carousel sensor (e.g. encoder) 134, RFID reader 140, button(s) 18, etc.

The electronics may also comprise a wireless circuitry 158 (e.g. Wifi, Bluetooth, etc.) for communicating directly or through the Cloud with an external device 160 (e.g. cell phone, tablet, laptop or other computing device). Cloud/Internet-based communication may also be exchanged with an external server 162 through wireless communication such as Wifi and/or cellular (3G, 4G, 5G, etc.).

External device 160 and/or server 162 may comprise application software for executing one or more functions detailed with respect to one or more dispensing device 10 components detailed above. Exchanged data and information may include, but is not limited to: patient profiles, medication, medication dosage, medication schedules, medication location in device, etc., and may be partially or wholly located locally at memory 156 or be located in the Cloud for system access through the phone, web, or desktop application. A limited or substantial subset of such data may exist on the dispensing device 10 for smooth and continuous operation in case of network failure.

One or more cameras 20 may be employed for verifying that a pill was dispensed and/or taking a picture of the user to verify the patient is the intended/correct patient. In one configuration, the user simply walks up to the dispensing device 10, and using facial recognition provided in application software 154 the dispensing device 10 administers the medication for the detected user. As the pill cup 24 is removed, the camera 20 may record a video of the user ingesting the medication. This may be stored in memory 156 or cloud, and serve as a log that the medication was taken and by the correct person.

One in exemplary method for dispensing medication, one or more medications stored in containers 32 are assigned a pill cap assembly 50 (with RFID 40 containing prescription data), and assembled with the appropriate pill cap assembly 50to form a pill cap/container assembly 30. The back cover 12b of device 10 is opened and one or more pill cap/container assemblies 30 are installed at any of the mating gear 108 locations on rotating platform 102. The back cover 12b is then closed, and the RFID reader 140 then reads the RFID 40 of each installed pill cap/container assembly 30. Data regarding the medication and or prescription is the stored in memory 156 and additional data from external device 160 and external server is acquired if necessary. The medication location on the carousel 100 is tracked, and dose/administration data is compiled for each medication, (e.g. patient, frequency and timing of administration, etc.). When it is time for a medication to be dispensed, the device 10 may send an alert/notification (e.g. one or more of a visual display, audible sound, push notifications/text message on external device (cell phone) 160). The user walks up to the unit, wherein dispensing to the correct user is authenticated through facial recognition, user created access code, or other means of identification (e.g. fingerprint reader, etc.).

Once authentication is completed, the dispensing device 10 commences administering the allocated pill. A command is sent to the carousel motor 130 to rotate the carousel assembly 100 to the desired pill cap/container assembly 30 that is containing the specified medication. Once at the correct slot (verification may be made via encoder 134), a command is sent to the dispensing motor 132 to activate gears 126 and 110/108 that rotate the pill capture head 52 to dispense the desired dose of medication. An internal sensor 136 (e.g. reflective IR light and photodiode) detects the pill as it passes through the dispensing channel 22. The device 10 then logs that a pill has been dispensed and/or provide a tally the number of pills that have been dispensed. The pill then falls into the pill cup 24 within dispensing region 26. Once pill(s) have been dispensed, the user can ingest them or leave them in cup 24 to get water, go to the bathroom, etc. The device 10 may be further programmed remind the user that pills are waiting to be taken, either through a sound or other push notifications or text messages, etc. Once the user removes the pill cup 24 the camera 20 starts recording a video. Video stops after a specified time or when the user places the pill cup back into its location. All pill dispensing events and associated data (e.g. user authentication, pills dispensed into the pill cup, pill cup removal, and the video log) are all logged and stored.

Figure 10:
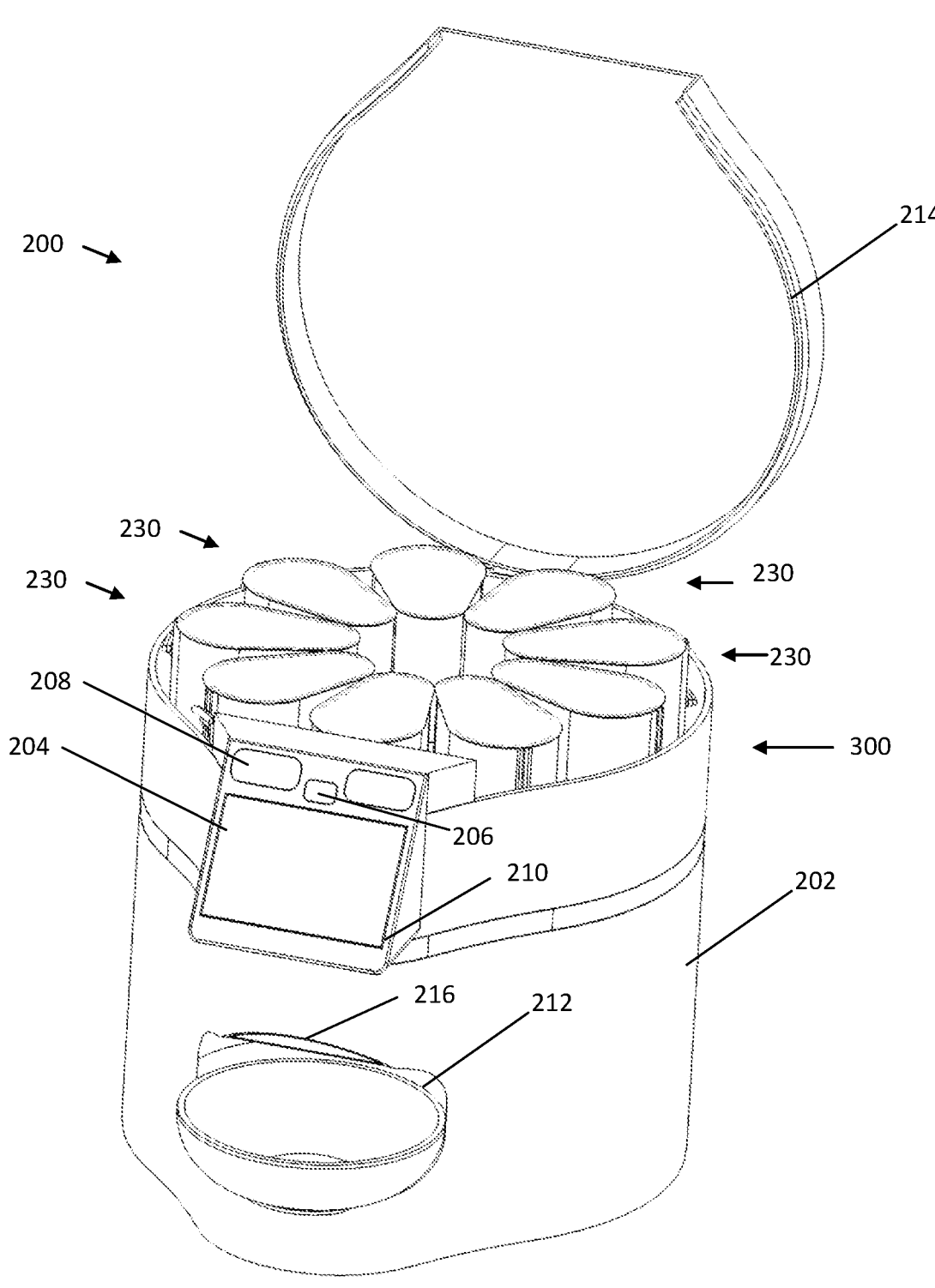
FIG. 10 shows perspective view of a cartridge-based medication adherence dispensing device in accordance with the present description.
Figure 11:
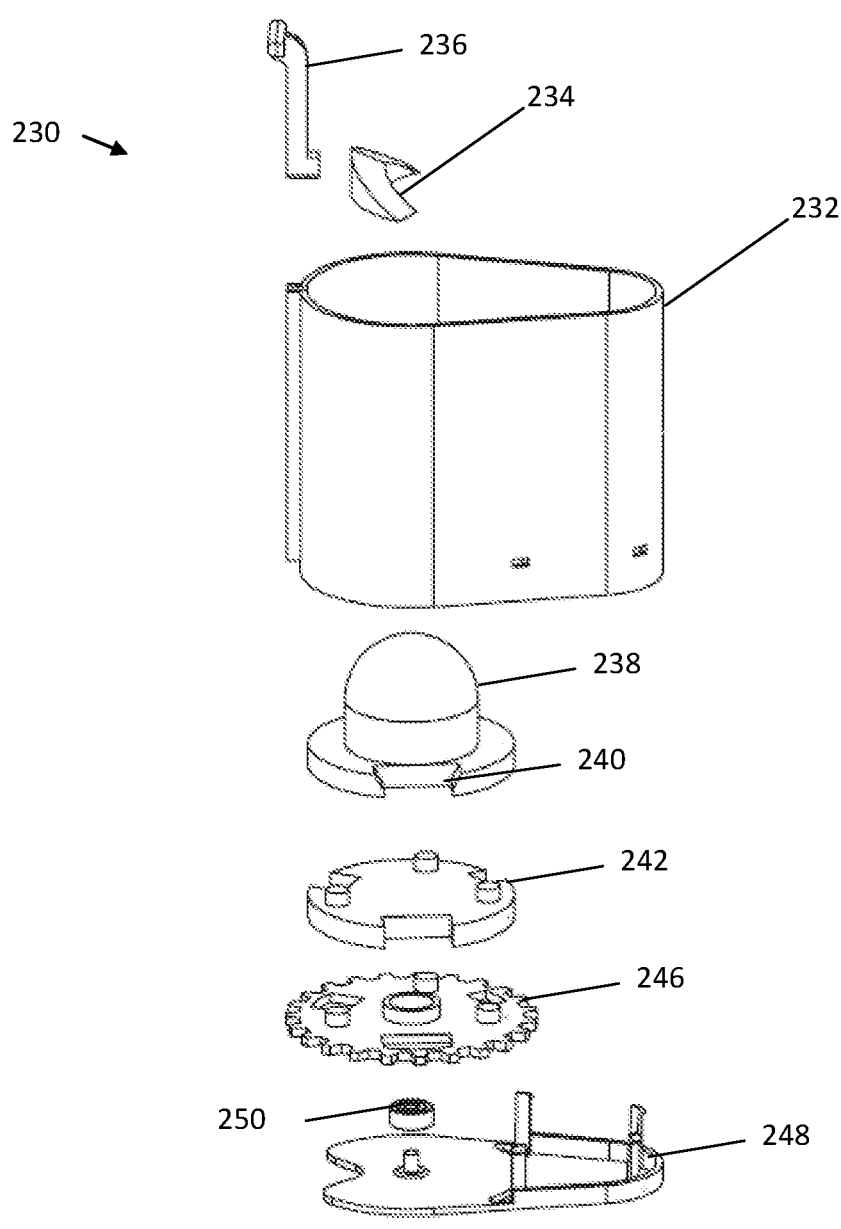
FIG. 11 shows an exploded perspective view of the medication cartridge assembly used for the device of FIG. 10.
Figure 12:
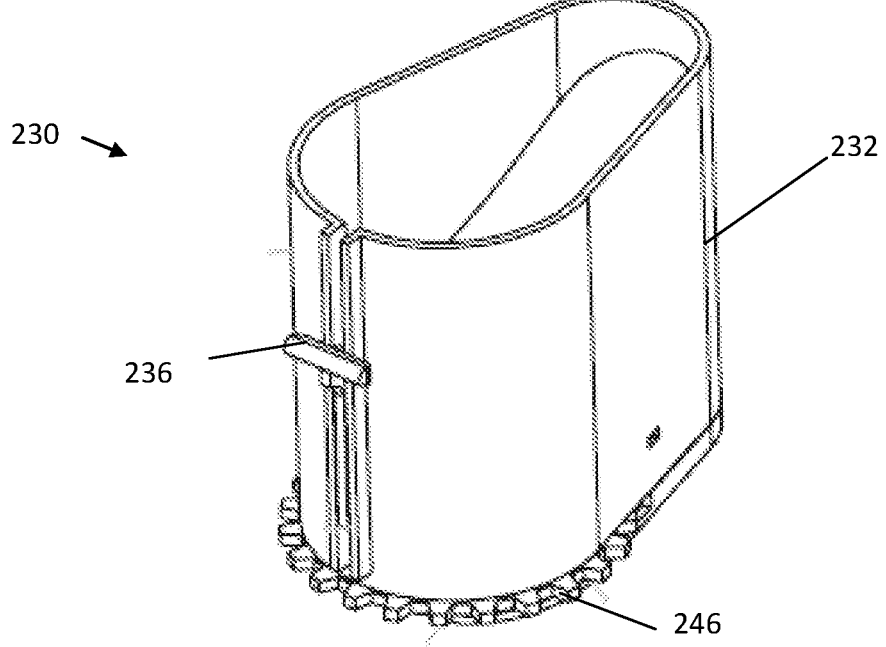
FIG. 12 shows an assembled perspective view of the medication cartridge assembly used for the device of FIG. 10.
Figure 13:
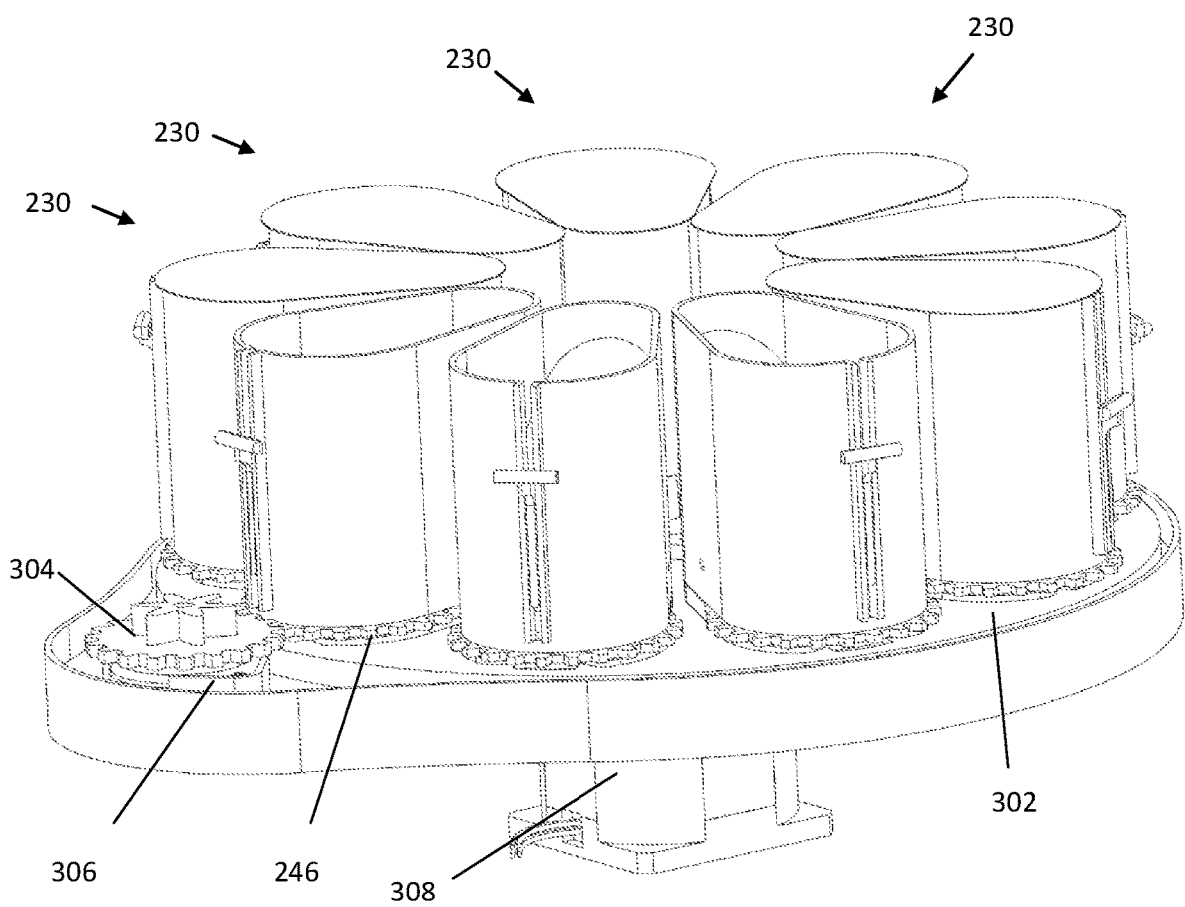
FIG. 13 shows a perspective view of a cartridge platform assembly for use with the device of FIG. 10.
Figure 14:
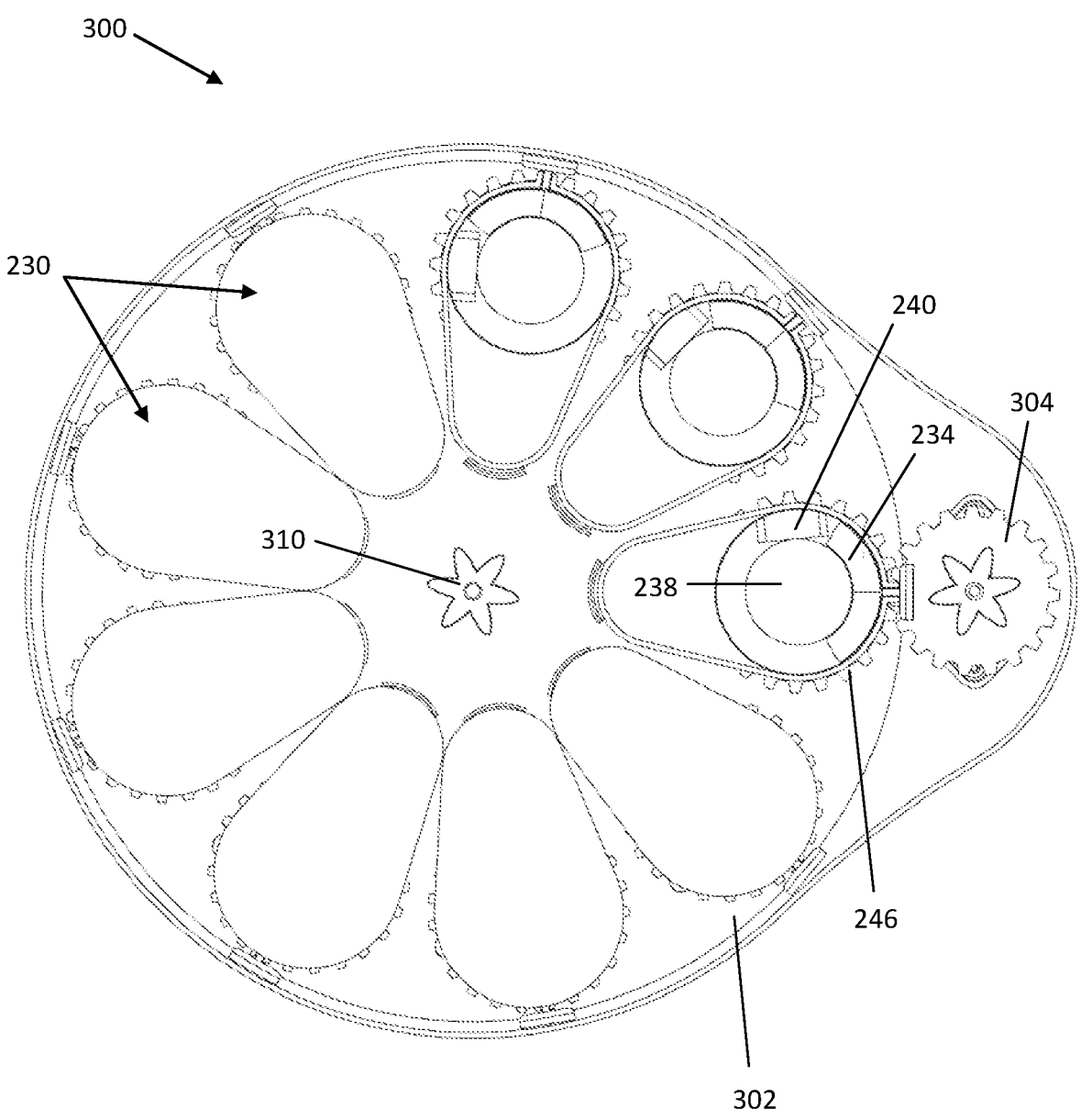
FIG. 14 is a top view of the cartridge platform assembly of FIG. 13.

FIG. 10 through FIG. 14 illustrate an alternative, cartridge-based medication adherence dispensing device 200 in accordance with the present description. FIG. 10 shows a perspective view of the cartridge-based medication adherence dispensing device 200. FIG. 11 shows an exploded perspective view of the medication cartridge assembly 230 for housing medication in device 200. FIG. 12 shows an assembled perspective view of the medication cartridge assembly 230. FIG. 13 and FIG. 14 show perspective view and top view, respectively, of a cartridge platform assembly 300 for use with dispensing device 200.

Referring to FIG. 10, medication adherence dispensing device 200 comprises an enclosure 202 having a central cavity that is accessed via a hinged top cover 214. The central cavity houses a rotating platform or carousel assembly 300 that rotatably supports a plurality of cartridge assemblies 230 (9 cartridges are shown in FIG. 10, although other configurations are contemplated) for holding medication. The housing 202 comprises a front panel 210 housing a display 204, one or more buttons 208 for user input, control or data entry, and camera 206. Front panel 210 may also comprise a logic board/controller (e.g. similar to controller 150 and components associated therewith detailed in FIG. 9) for controlling and or receiving input data from the various components of dispensing device 200, including motors, sensors, cameras, readers, external devices and servers, etc. A dispensing cup 212 is provided for dispensing medication. A scanner 216 (e.g. bar code scanner, RFID reader, camera, like scanning device, or combination thereof) may be dispose at the top of the dispensing cup 212.

Referring now to FIG. 11 and FIG. 12, each cartridge assembly 230 is configured for the efficient and accurate dispensing of medications, and comprises an enclosure 232 that houses the medication and respective components. One or more of the components of the cartridge assembly may be specifically configured (e.g. size and shape) for a particular mediation to be dispensed. Inside the enclosure 232 is disposed a pill capture head 238 that is sized according to one or more dimensions (e.g. width) of the medication so that only one pill may fit between the inner pill capture head and the cartridge wall 232. One or more pill spacers 242 may also be included, with the number of spacers depending on the height of the pill. The pill capture head 238 and pill spacers 242 are preferably press fit together (with protrusions/recesses to inhibit rotation with respect to each other) and when rotated allow only a single pill to be picked up and dispensed. A pill capture gear 246 is coupled to and disposed under spacer 242/capture head 238, and is rotatably mounted to a pin via bearing 250 on a bottom platform 248 of the housing.

The pill capture gear 246 is configured to mate with the control gear 304 on the device 200 (see FIG. 13 and FIG. 14) when the selected cartridge assembly 230 is positioned at the control gear 304. This affects the rotation of the pill capture head 238 to pick up a pill for dispensing. A sweeper 234 is located and affixed directly above the pill capture head 238 and over a hole/slot in bottom platform 248 that allows the pills to fall out of the cartridge 230 once the pill is caught in offset slot 240 of the capture head 238. The sweeper 234 is configured for blocking and redirecting the pills in the enclosure so only one pill falls through and is dispensed at a time.

In a preferred embodiment, each cartridge 230 comprises a barcode label and/or have an RFID chip (both not shown) attached to the cartridge (e.g. via adhesive or like attachment means). The barcode or RFID may include information regarding the prescription and/or patient, including but not limited to information from the fulfillment facility regarding the type of medication, dosage, number of pills, etc.

Referring to FIG. 13 and FIG. 14, cartridge(s) 230 mate with the rotating platform 302 inside the dispensing device 200 cavity. In a preferred embodiment, a control gear 304 is affixed to a first (pill dispensing) motor 306 and the rotating platform 302 is affixed to a second (carousel) motor 308. The cartridge(s) 230 are scanned (e.g. bar code, RFID) and placed in a specific location on the rotating platform and/or the scanner216 collects the information and registers the location of the cartridge(s) 230 on the platform 302. In one embodiment, the location of the cartridges 230 is tracked via a magnet (not shown) that is positioned at a specified location on the rotating platform 302. The known location of the magnet allows a corresponding sensor (e.g. encoder/sensor 134 in FIG. 9) to identify the position of the magnet and relative position of the cartridge(s) 230. This allows the dispensing device 200 to log where each medication is located in order to move to the correct position to dispense the appropriate medication.

In order to dispense a pill/medication, upon activation of the carousel motor 308, the rotating platform 302 rotates (via gear 310) to place a specific cartridge 230 in the "dispense" position, e.g. where the gear 246 of the cartridge is now mated with the control gear 304. Upon activation of the pill dispensing motor 306, control gear 304 then rotates the cartridge gear 246 to rotate the pill capture head 238 to pick up a pill in the capture slot 240, and then keeps rotating until the pill falls out from the bottom of the cartridge 230. The pill then follows the channel and gets placed in the pill cup 212 located on the exterior of the device 200 where the user can then take his/her medication.

One or more cameras 206/216 may also be included for verifying that a pill was dispensed and/or taking a picture of the user to verify the patient is the correct person to dispense the pills for. In one configuration, the user merely walks up to the device and using an identification means (e.g. facial recognition (via camera 206), voice recognition (via microphone-not shown), fingerprint recognition (via camera/scanner) or the like), and the dispensing device 200 identifies the user and dispenses the medication for the detected user based on the indicated medication to be dispensed at the time, ensuring chain of custody.

It is also appreciated that the RFID reader 140/barcode scanner 216 may be implemented to verify/track compliance with medications external to (i.e. not dispensed from) the dispensing device 10/200. For example, a patient may scan the barcode on an inhaler (not shown) and use the device cameras 20/206 to track adherence. The dispensing device 10/200 may also include functionality to include a travel portion having a portable form factor to dispense medications. The application software 154 may include functionality to facilitate proper setup of the dispensing device 10/200 and operation of the device with the user. Various processes may be implemented as instructions or code implemented within the application software 154 as a cell-phone interface, or on the screen/display 16/204 of the dispensing device 10/200.

Application software 154 may be configured for interfacing with the dispensing device 10/200, including but not limited to: adding new medications to dispense, setting the schedule at which the medications will be dispensed, entering patient information, confirming the dispensing of said medication, etc. Some or all data and information including, but not limited to, patient profiles, medication, medication dosage, medication schedules, medication location in dispensing device, etc. may be located in the cloud for easy access by the user through the phone, web, or desktop application. A limited subset of this data may exist on the device for smooth and continuous operation in case of network failure.

Application software 154 may include functionality for device 10/200 connection and home screen processes in accordance with external devices or screen views comprising: 1) application loading screen; 2) first time loading to connect device before using the application (one button labeled "Connect a Device"); 3) automatically search for a device based on the Wi-Fi network (the dispensing device 10/200may comprise a unique recognizable Wi-Fi name as an examplehido_PB_(Unique identifier)); 4) home Wi-Fi network name and password; 5) Wi-Fi network drop down menu with available networks shown; 6) Wi-Fi password manual entry; 7) connect button to initiate connection; 8) connection screen for while the network is being setup and device is connecting to home Wi-Fi; 9) home screen once device has been connected, 10) graphical user interface including a scroll wheel illustrating current medications that have been added.

Application software 154 may include functionality for adding medication processes as the following screens 1) home screen within formation about how to add a medication; 2) confirmation screen once barcode scanner reads medication barcode; 3) back to the home screen; 4) confirmation screen; 5) if medication is confirmed, a description is provides of how to add the medication to the carousel, (e.g. load into slot 1 on platform); 6) additional instructions may be included, e.g. the medication needs to be poured into cartridge; 7) once loaded, the medication information will show up in the scroll wheel (e.g. as slot 1).

Application software 154 may include functionality for a menu screen having the following screen views: 1) side menu button showing the menu; 2) selectable options including medications list, schedule, and history, etc.; 3) home button back to the home screen; 4) home screen; 5) display listing available medications; 6) medication selected to show more information about the medication.

Application software 154 may include functionality for additional menu screen views such as: 1) home screen with schedule selected; 2) display of the default scheduled labels/groupings of Morning, Afternoon, and Evening; 3) screen allowing changing the time of these defaults and/or add medications to the schedule by selecting the label/grouping; 4) "add to schedule" selected for creating other dispense times within the schedule by selecting add to schedule; 5) screen for entry of new label; 6) screen for selection of time this label/grouping will be dispensed; 7) display showing new label/grouping added to the schedule screen; 8) home screen with history selected; 9) list view of all the days the schedule had been active; 10) month view and select the day for going back in time farther; 11) once a day has been selected, display shows the schedule for that day and the medications that were taken or possibly missed.

It is appreciated that while the embodiments disclosed above provide preferred systems and methods for dispensing medication, the specific geometries and mechanical configurations may be varied as appropriate. For example, linear actuation assemblies (rather than rotating) may be employed to drive a linear array of containments comprising cartridges or pill cap/container assemblies. Any number of containments are contemplated, in various sizes. Gears may also be interchangeably replaced with other actuation means (e.g. linkages, etc.) to drive motion necessary for moving the pill heads or other parts associated with dispensing the pills.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other program-mable processing apparatus to produce a computer-imple-mented process such that the instructions which execute on the computer processor or other programmable processing apparatus provide steps for implementing the functions specified in the block(s) of the flowchart(s), procedure(s) algorithm(s), step(s), operation(s), formula (e), or computa-tional depiction(s).

It will further be appreciated that the terms "program-ming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used syn-onymously to denote a device capable of executing the instructions and communicating with input/output interfaces and/or peripheral devices, and that the terms processor, hardware processor, computer processor, CPU, and com-puter are intended to encompass single or multiple devices, single core and multicore devices, and variations thereof.

From the description herein, it will be appreciated that that the present disclosure encompasses multiple embodi-ments which include, but are not limited to, the following:

1. An apparatus for dispensing medication or supple-ments, comprising: a platform configured for receiving one or more medication dispensing containments, the medica-tion containments configured for housing a plurality of pills comprising medication or supplements; a scanner or user input for identifying the one or more medication contain-ments and receiving data specific to the medication or supplements provided therein; the medication containment comprising a lower surface having a dispensing opening and pill capture head sized according to at least one dimension of the plurality of pills contained therein, and a medication sweeper disposed above the pill capture head and between the plurality of pills so as to selectively direct is single pill out the dispensing opening, while blocking a remainder of the plurality of pills in the containment; a first gear coupled to the pill capture head and medication sweeper such that rotation of the gear affects rotation of the pill capture head with respect to the medication sweeper to dispense the single pill; and a motor coupled to the first gear; the motor configured for receiving commands to affect said activation and dispense the single pill.

2. The apparatus or method of any of the subsequent or previous embodiments, wherein the said motor activation is timed according a schedule determined from the data spe-cific to the medication or supplements acquired from the identified medication containment.

14

3. The apparatus or method of any of the subsequent or previous embodiments, wherein the platform comprises a rotating platform for receiving a plurality of medication containments, the apparatus further comprising: a second motor coupled to the rotating platform; the second motor configured to rotate the platform such that a specified medication containment among the plurality of contain-ments aligns with the first gear to dispense medication disposed within the specified medication containment.

4. The apparatus or method of any of the subsequent or previous embodiments, wherein the scanner comprises a barcode scanner or RFID receiver configured to read a barcode or RFID tag on the one or more medication con-tainments.

5. The apparatus or method of any of the subsequent or previous embodiments, further comprising: one or more cameras or sensors configured to detect one or more of: dispensing of the medication, consumption of the medica-tion, and identification of a user consuming the medication.

6. The apparatus or method of any of the subsequent or previous embodiments, further comprising: one or more sensors coupled to the rotating platform, the one or more sensors configured to provide location data of the rotating platform so as to identify the one or more containments received thereon.

7. The apparatus or method of any of the subsequent or previous embodiments:
   wherein the containment comprises an inner cavity hous-ing the plurality of pills; and
   wherein the medication sweeper is fixed in relation to the inner cavity while the pill dispensing head rotates within the cavity.

8. The apparatus or method of any of the subsequent or previous embodiments: wherein the one or more medication dispensing containments comprises an existing pill con-tainer housing the plurality of pills and a pill cap assembly configured to secure to an opening of the container; wherein the pill capture head and medication sweeper are disposed within the pill cap assembly.

9. The apparatus or method of any of the subsequent or previous embodiments, wherein the medication head is disposed at an elevated location above the dispensing open-ing of the containment and the pill capture head has head portion having a first diameter at a specified distance from an inner wall of the cavity such that rotation of the pill capture head allows only the single pill to be dispensed out of the dispensing opening.

10. The apparatus or method of any of the subsequent or previous embodiments: wherein the pill capture head has a base portion coupled to the head portion, the base portion having a second diameter sized to be similar or slightly smaller than the inner wall of the cavity and an offset slot sized to receive the single pill; and wherein the pill capture head carries the single pill in the offset slot until it rotates over the dispensing opening, upon which the single pill is dispensed out the dispensing opening.

11. The apparatus or method of any of the subsequent or previous embodiments, further comprising: a processor coupled to the first motor and scanner; and a non-transitory memory storing instructions executable by the processor; wherein said instructions, when executed by the processor, perform steps comprising: operating the scanner and receiv-ing said data specific to the medication or supplements provided within the medication containment; and operating the first motor to dispense said medication according instructions received from said data.

12. The apparatus or method of any of the subsequent or previous embodiments, the instructions further configured for coupling the apparatus to an external device or web interface to allow for scheduling of dispensing of the medication or supplements.

13. A method for dispensing medication or supplements, comprising: housing a plurality of pills comprising medication or supplements within one or more medication dispensing containments; wherein the medication containment comprises a lower surface having a dispensing opening and pill capture head sized according to at least one dimension of the plurality of pills contained therein, and a medication sweeper disposed above the pill capture head and between the plurality of pills; receiving one or more medication dispensing containments on a platform, scanning or receiving input for identifying the one or more medication containments and acquiring data specific to the medication or supplements provided therein; and affecting rotation of the pill capture head with respect to the medication sweeper to selectively direct is single pill out the dispensing opening, while blocking a remainder of the plurality of pills in the containment to dispense the singe pill for consumption.

14. The apparatus or method of any of the subsequent or previous embodiments, wherein dispensing of the single pill is timed according a schedule determined from the data specific to the medication or supplements acquired from the identified medication containment.

15. The apparatus or method of any of the subsequent or previous embodiments, wherein the platform comprises a rotating platform and a plurality of medication containments are received on the platform, the method further comprising: rotating the platform such that a specified medication containment among the plurality of containments aligns with a dispensing location for affecting the rotation of the pill capture head to dispense medication disposed within the specified medication containment.

16. The apparatus or method of any of the subsequent or previous embodiments: herein scanning or receiving input comprises scanning a barcode or RFID tag on the one or more medication containments to acquire the data specific to the medication or supplements; and automatically dispensing the single pill according to the schedule determined from the data specific to the medication or supplements 17. The apparatus or method of any of the subsequent or previous embodiments: wherein housing a plurality of pills comprises assembling and securing a pill cap assembly to an open end of an existing pill container housing the plurality of pills; and wherein the pill capture head and medication sweeper are disposed within the pill cap assembly.

18. The apparatus or method of any of the subsequent or previous embodiments: wherein the containment comprises an inner cavity housing the plurality of pills and wherein the medication head is disposed at an elevated location above the dispensing opening of the containment and the pill capture head has a head portion having a first diameter at a specified distance from an inner wall of the cavity; and wherein affecting rotation of the pill capture head comprises rotating the pill dispensing head within the cavity while the medication sweeper is fixed in relation to the inner cavity so that only the single pill is dispensed out the dispensing opening.

19. The apparatus or method of any of the subsequent or previous embodiments: wherein the pill capture head has a base portion coupled to the head portion, the base portion having a second diameter sized to be similar or slightly smaller than the inner wall of the cavity and an offset slot sized to receive the single pill; and wherein the pill capture head carries the single pill in the offset slot until it rotates over the dispensing opening, upon which the single pill is dispensed out the dispensing opening.

20. The apparatus or method of any of the subsequent or previous embodiments, further comprising: coupling the platform to an external device or web interface; and scheduling one or more events for automatic dispensing of the medication or supplements.

21. An apparatus for dispensing medication or supplements, comprising: a platform configured for receiving one or more medication cartridges, the medication cartridges configured for housing a plurality of pills comprising medication or supplements; a scanner or user input for identifying the one or more medication cartridges and receiving data specific to the medication or supplements provided therein; the medication cartridge comprising a pill capture head sized according to a width of the pills and a medication sweeper is configured for blocking and redirecting the pills in the cartridge so only one pill falls through and is dispensed at a time; a control gear coupled to the pill capture head and medication sweeper such that rotation of the control gear affects activation of the pill capture head and medication sweeper to dispense one of the pills; a motor coupled to the control gear; the motor configured for receiving commands to affect said activation and dispense a pill according a schedule determined from data specific to the data from the identified medication cartridge.

22. The apparatus or method of any preceding or subsequent embodiment, wherein the platform comprises a rotating platform for receiving a plurality of medication cartridges, the apparatus further comprising: a second motor coupled to the rotating platform; the second motor configured to rotate the platform such that a specified medication cartridge among the plurality of cartridges aligns with the control gear to dispense medication disposed within the specified medication cartridge.

23. The apparatus or method of any preceding or subsequent embodiment, wherein the scanner comprises a barcode scanner or RFID receiver configured to read a barcode or RFID tag on the one or more medication cartridges.

24. The apparatus or method of any preceding or subsequent embodiment, further comprising: one or more cameras configured to detect one or more of: dispensing of the medication, consumption of the medication, and identification of a user consuming the medication.

25. The apparatus or method of any preceding or subsequent embodiment, further comprising: a processor coupled to the first motor and scanner; and a non-transitory memory storing instructions executable by the processor; wherein said instructions, when executed by the processor, perform steps comprising: operating the scanner and receiving said data specific to the medication or supplements provided within the medication cartridge; and operating the first motor to dispense said medication according instructions received from said data.

26. The apparatus or method of any preceding or subsequent embodiment, the instructions further configured for coupling the apparatus to an external device or web interface.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to #10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for dispensing medication or supplements, comprising:
housing a plurality of pills comprising medication or supplements within one or more medication dispensing containments;
wherein the medication containment comprises a lower surface having a dispensing opening and pill capture head sized according to at least one dimension of the plurality of pills contained therein, and a medication sweeper disposed above the pill capture head and between the plurality of pills;
receiving one or more medication dispensing containments on a platform;

18 scanning or receiving input for identifying the one or more medication containments and acquiring data specific to the medication or supplements provided therein;
according to instructions provided in the acquired data, generating an ingestion schedule for the medication or supplements; and
automatically dispensing the single pill according to the ingestion schedule by affecting rotation of the pill capture head with respect to the medication sweeper to selectively direct the single pill out the dispensing opening, while blocking a remainder of the plurality of pills in the containment to dispense the singe pill for consumption.

2. The method of claim 1, wherein dispensing of the single pill is timed according a schedule determined from the data specific to the medication or supplements acquired from the identified medication containment.

3. The method of claim 1, wherein the platform comprises a rotating platform and a plurality of medication containments are received on the platform, the method further comprising:
rotating the platform such that a specified medication containment among the plurality of containments aligns with a dispensing location for affecting the rotation of the pill capture head to dispense medication disposed within the specified medication containment.

4. The method of claim 2:
wherein scanning or receiving input comprises scanning a barcode or RFID tag on the one or more medication containments to acquire the data specific to the medication or supplements; and
automatically dispensing the single pill according to the schedule determined from the data specific to the medication or supplements.

5. The method of claim 1:
wherein housing a plurality of pills comprises assembling and securing a pill cap assembly to an open end of an existing pill container housing the plurality of pills; and
wherein the pill capture head and medication sweeper are disposed within the pill cap assembly.

6. The method of claim 5:
wherein the containment comprises an inner cavity housing the plurality of pills and wherein the medication sweeper is disposed at an elevated location above the dispensing opening of the containment and the pill capture head has a head portion having a first diameter at a specified distance from an inner wall of the cavity; and
wherein affecting rotation of the pill capture head comprises rotating the pill capture head within the cavity while the medication sweeper is fixed in relation to the inner cavity so that only the single pill is dispensed out the dispensing opening.

7. The method of claim 6:
wherein the pill capture head has a base portion coupled to the head portion, the base portion having a second diameter sized to be similar or slightly smaller than the inner wall of the cavity and an offset slot sized to receive the single pill; and
wherein the pill capture head carries the single pill in the offset slot until it rotates over the dispensing opening, upon which the single pill is dispensed out the dispensing opening.

8. The method of claim 1, further comprising:
coupling the platform to an external device or web interface; and scheduling one or more events for automatic dispensing of the medication or supplements.

9. The method of claim 1, wherein after scanning or receiving input, the method further comprises:

logging a location of the medication containment with respect to other medication containments loaded on the platform, the medication containments each having dedicated medications for dispensing to the patient; and said location being used to identify a particular medication containment for dispensing according to the acquired instructions.

10. A method for dispensing medication or supplements, comprising:

housing a plurality of pills comprising medication or supplements within one or more medication dispensing containments;

wherein the medication containment comprises a lower surface having a dispensing opening and pill capture head sized according to at least one dimension of the plurality of pills contained therein, and a medication sweeper disposed above the pill capture head and between the plurality of pills;

receiving one or more medication dispensing containments on a platform;

scanning or receiving input for identifying the one or more medication containments and acquiring data specific to the medication or supplements provided therein; and according to instructions provided in the acquired data, automatically selecting a particular medication containment from among a plurality of medication containments each containing a different medication from the other containments and dispensing the single pill according to a schedule determined from the acquired instructions by affecting motion of the pill capture head with respect to the medication sweeper to selectively direct a single pill out the dispensing opening, while blocking a remainder of the plurality of pills in the containment to dispense the singe pill for consumption.

11. The method of claim 10, wherein after scanning or receiving input, the method further comprises:

logging a location of the medication containment with respect to other medication containments loaded on the platform, the medication containments each having dedicated medications for dispensing to the patient; and said location being used to identify a particular medication containment for dispensing according to the acquired instructions.

12. The method of claim 10, wherein dispensing of the single pill is timed according a schedule determined from the data specific to the medication or supplements acquired from the identified medication containment.

13. The method of claim 10, wherein the platform comprises a rotating platform and a plurality of medication containments are received on the platform, the method further comprising:

rotating the platform such that a specified medication containment among the plurality of containments aligns with a dispensing location for affecting the rotation of the pill capture head to dispense medication disposed within the specified medication containment.

14. The method of claim 12:

wherein scanning or receiving input comprises scanning a barcode or RFID tag on the one or more medication containments to acquire the data specific to the medication or supplements; and automatically dispensing the single pill according to the schedule determined from the data specific to the medication or supplements.

15. The method of claim 10:

wherein housing a plurality of pills comprises assembling and securing a pill cap assembly to an open end of an existing pill container housing the plurality of pills; and wherein the pill capture head and medication sweeper are disposed within the pill cap assembly.

16. The method of claim 15:

wherein the containment comprises an inner cavity housing the plurality of pills and wherein the medication head is disposed at an elevated location above the dispensing opening of the containment and the pill capture head has a head portion having a first diameter at a specified distance from an inner wall of the cavity; and wherein affecting rotation of the pill capture head comprises rotating the pill dispensing head within the cavity while the medication sweeper is fixed in relation to the inner cavity so that only the single pill is dispensed out the dispensing opening.

17. The method of claim 16:

wherein the pill capture head has a base portion coupled to the head portion, the base portion having a second diameter sized to be similar or slightly smaller than the inner wall of the cavity and an offset slot sized to receive the single pill; and wherein the pill capture head carries the single pill in the offset slot until it rotates over the dispensing opening, upon which the single pill is dispensed out the dispensing opening.

18. The method of claim 10, further comprising:

coupling the platform to an external device or web interface; and scheduling one or more events for automatic dispensing of the medication or supplements.

19. A method for dispensing medication or supplements, comprising:

housing a plurality of pills comprising medication or supplements within one or more medication dispensing containments, each of the medication dispensing containments configured to house distinct medications or medications for dispensing to a patient;

wherein the medication containment comprises a lower surface having a dispensing opening and pill capture head sized according to at least one dimension of the plurality of pills contained therein, and a medication sweeper disposed above the pill capture head and between the plurality of pills;

receiving a plurality of medication dispensing containments on a platform;

scanning or receiving input for identifying each of the medication containments and acquiring data specific to the medication or supplements provided therein;

logging a location of the received medication containments on the platform in relation to other medication containments loaded on to the platform; and according to instructions provided in the acquired data, automatically selecting a particular medication containment from among a plurality of medication containments and dispensing the single pill according to a schedule determined from the acquired instructions affecting motion of the pill capture head with respect to the medication sweeper to selectively direct a single pill out the dispensing opening, while blocking a remainder of the plurality of pills in the containment to dispense the singe pill for consumption.

20. The method of claim 19, further comprising:

according to instructions provided in the acquired data, generating an ingestion schedule for the medication or supplements; and wherein the single pill is automatically dispensed according to the ingestion schedule.

\*  \*  \*  \*  \*